United States Patent [19]

Lee et al.

[11] Patent Number: 5,130,232
[45] Date of Patent: Jul. 14, 1992

[54] MONOCLONAL ANTIBODY IMMUNOASSAY KIT FOR AVIAN RETICULOENDOTHELIOSIS VIRUS

[75] Inventors: Lucy F. Lee, East Lansing, Mich.; Zhizhong Cui, Yangshou, China; Richard L. Witter, Okemos, Mich.

[73] Assignee: The United States of America as represented by the Secretary of Agriculture, Washington, D.C.

[21] Appl. No.: 536,860

[22] Filed: Jun. 12, 1990

[51] Int. Cl.$^5$ .............. C12Q 1/70; C12Q 1/00; G01N 33/53; C12N 5/00; A61K 35/14; C07K 3/00; C07K 13/00; C07K 15/00

[52] U.S. Cl. ................................ 435/5; 435/7.92; 435/973; 435/240.27; 436/501; 436/811; 530/388.35; 530/389.4

[58] Field of Search ............... 435/5, 7.9, 960, 973, 435/240.27; 436/501, 811; 530/384

[56] References Cited

U.S. PATENT DOCUMENTS 4,514,505 4/1985 Cranfield et al. ............... 436/500

OTHER PUBLICATIONS

Cho (1983) Cytopathic Effects and Focus Formation-Avian Dis 27:261-270.

Cui et al. (1986) Monoclonal Antibodies Against AEV-J. Immunol 136:4237-42.

Cui et al. (1988) Monoclonal Ab. Mediated Elisa-Avian Disease 32: 32-40.

Zhi-Zhong Cui et al., "Monoclonal Antibodies Against Avian Reticuloendotheliosis Virus: Identification of Strain-Specific and Strain-Common Epitopes", J. Immunol. 136(11): 4237-4242 (Jun. 1, 1986).

Zhizhong Cui et al., "Monoclonal-Antibody-Mediated Enzyme-Linked Immunosorbent Assay for Detection of Reticuloendotheliosis Viruses", Avian Dis. 32: 32-40 (1988).

*Primary Examiner*—Christine M. Nucker
*Assistant Examiner*—D. R. Preston
*Attorney, Agent, or Firm*—M. Howard Silverstein; Curtis P. Ribando; John D. Fado

[57] ABSTRACT

The combination of monoclonal antibodies 11A25 and 11E32, which recognize two distinct antigenic sites on the 62-kd glycoprotein of reticuloendotheliosis virus (REV) in ELISA, enables an increase in the sensitivity of an ELISA assay for subtype 2 REV over what was heretofore possible. The combination of MAbs is useful for diagnosing REV antigen and antibody in poultry flocks and for detecting new strains and variants of the viral subtype.

9 Claims, No Drawings

MONOCLONAL ANTIBODY IMMUNOASSAY KIT FOR AVIAN RETICULOENDOTHELIOSIS VIRUS

BACKGROUND OF THE INVENTION

1. Field of the Invention

Reticuloendotheliosis viruses (REVs) are a group of serologically related retroviruses antigenically distinct from avian leukosis retroviruses (ALVs). REV isolates have been obtained from turkeys, pheasants, chickens, and ducks. These isolates have been classified into three subtypes based on cross neutralization with polyclonal antisera and indirect immunofluorescence with monoclonal antibodies. Representative REVs include strain T (subtype 1), chick syncytial (CS; subtype 3), spleen necrosis (SN; subtype 2), and duck infectious anemia (DIA; subtype 2) viruses. Using a combination of monoclonal antibodies (MAbs) in indirect fluorescent-antibody test and in cross-neutralization tests with chicken sera, Chen et al. [Arch. Virol. 93: 233–245 (1987)] have defined three antigenic subtypes among 26 REV isolates studied.

REV causes immunodepression, neoplams, and runting in chickens. It has also been implicated in contaminated Marek's disease vaccines. The occurrence of REV in turkeys and the presence of REV antibodies in Japanese quails with lymphoproliferative disease suggest that REV infection may be widespread. Moreover, morphologic similarities to peripheral nerve lesions associated with Marek's disease necessitates specific diagnostic assays to provide unequivocal evidence of REV infection.

Although Cho [Avian Dis. 27: 261–270 (1983)] reported focus formation of REV in quail fibroblasts, infection of REV is not consistently cytopathic in chicken cells.

2. Description of the Prior Art

Witter et al. [J. Natl. Cancer Inst. 45: 567–577 (1970)] have reported on an immunofluorescence assay for REV, and a specific REV micro-complement-fixation test has been reported by Smith et al. [Avian Dis. 21: 612–622 (1977)]. However, both tests require adequate REV replication and amplification and are therefore cumbersome for mass screening of flocks. Ianconescu [Avian Pathol. 6: 259–267 (1977)] and Bagust [Avian Pathol. 8: 375–389 (1979)] used agar gel precipitation (AGP) to detect REV in experimentally infected chicken plasmas and sera, but the limits of sensitivity were not reported. AGP is relatively insensitive and also requires REV propagation.

Cui et al. [Avian Dis. 32: 32–40 (1988)] have described an enzyme-linked immunosorbent assay (ELISA) which uses a mixture of MCAs prepared against a 62-kilodalton (kd) REV envelope glycoprotein (gp 62) to detect REV antigen. The MAbs 11A25 and 11C237 each recognize a different epitope, so that the combination of the two in ELISA result in enhanced sensitivity of detection. However, unlike MAb 11A25, which is cross-reactive with all three subtypes, MAb 11C237 reacts only with subtypes 1 and 3.

A successful monoclonal-mediated ELISA must meet several criteria including the ability of the MAb to recognize a major common epitope of the virus, the ability of the MAb to recognize different epitopes on the same protein molecule, and the ability of these MAbs when combined to give a synergistic additive effect to enhance sensitivity.

SUMMARY OF THE INVENTION

We have developed an improvement over the monoclonal antibody-mediated ELISA of Cui et al. for detecting REV antigen in chicken and turkey flocks. The assay involves the use of a mixture of two MAbs prepared against a 62-kd REV envelope glycoprotein (gp 62) for antigen capture, rabbit anti-REV serum as detection antibody, and peroxidase-conjugated anti-rabbit IgG as indicator antibody. The MAbs (11A25 and 11E32) recognize two distinct antigenic sites on the REV 62-kd glycoprotein in competitive ELISA. One of the MAbs, 11A25, is the same as that used by Cui et al. The other is a novel MAb which is referred to as 11E32 and has a broader range of reactivity than 11C237. Both 11A25 and 11E32 cross-react with three subtypes of REV tested. The ELISA is also useful for detecting antibody to the REV antigen. The novel combination of MAbs will result in an increase in the sensitivity of an ELISA assay for subtype 2 REV over what was heretofore possible. It will also enable the detection of new strains and variants of subtype 2 REV.

In accordance with this discovery, it is an object of this invention to use monoclonal antibody-mediated ELISA as a kit for diagnosis of REV infection in individual birds and for detecting REV antigen and antibody in poultry flocks.

It is also the object of the invention to use these two MAbs for capturing REV antigen.

Another object of the invention is to provide REV-specific MAb useful in avian immunological research and pathological diagnosis.

Still another object of the invention is to provide hybridoma cell lines for generating the subject MAbs.

Other objects and advantages of the invention will become readily apparent from the ensuing description.

DEPOSIT OF BIOLOGICAL MATERIAL

The cloned hybridoma cell lines 11A25 and 11E32 were deposited on Apr. 26, 1990, under the conditions of the Budapest Treaty with the American Type Culture Collection, Rockville, MD, and have been assigned Accession numbers ATCC HB 10440 and ATCC HB 10441, respectively.

GLOSSARY

For purposes of this invention, the following standard abbreviations used herein have been defined below.

| ABBREVIATIONS | |
|---|---|
| AGP = | agar gel precipitation |
| ALV = | avian leukosis virus (exogenous oncogenic virus) |
| BSA = | bovine serum albumin |
| CEF = | chicken embryo fibroblast |
| CF = | complement fixation |
| CS = | chick syncytial |
| CSV = | chick syncytial virus (strain of REV) |
| DIA = | duck infectious anemia |
| DIAV = | duck infectious anemia virus (strain of REV) |
| DMEM = | Dulbecco's modified eagle medium |
| ELISA = | enzyme-linked immunosorbent assay |
| FFU = | focus forming units |
| gp = | glycoprotein |
| IF = | immunofluorescence |
| IgG = | immunoglobulin type G |
| IP = | intraperitoneal |
| kd = | kilodalton |
| LLV = | lymphoid leukosis virus |
| MAb = | monoclonal antibody |

-continued

| ABBREVIATIONS | |
|---|---|
| MDV = | Marek's disease virus |
| PBS = | phosphate-buffered saline |
| REV = | reticuloendotheliosis virus |
| SDS = | sodium dodecyl sulfate |
| SPF = | chicken line |
| T = | strain of REV |
| T-CEF = | REV strain T-infected CEF |

DETAILED DESCRIPTION OF THE INVENTION

The development of an antigen detection kit for REV in accordance with the invention is a multiple-step procedure including: (1) the development of hybridoma cell lines which produce MAbs having the desired specificity and high affinity for capturing REV protein antigen; (2) preparation of the MAbs; and (3) incorporation of these antibodies into a simple and specific ELISA procedure.

The hybridoma cell lines, 11A25 and 11E32, were generated at the Agricultural Research Service Regional Poultry Laboratory in East Lansing, MI, by fusing mouse myeloma cells NS-1 with splenic B-lymphocytes from BALB/c mice previously immunized with purified virions of strain T REV. The fusion of the cells using polyethylene glycol and the selection of hybrids producing MAbs were conducted by standard methods according to the published procedure of Lee et al. [J. Immunol. 130: 1003-1006 (1983)], herein incorporated by reference. While the general method of obtaining MAb-producing hybridoma cells is well established, the technology is unpredictable in terms of isolating a hybridoma line producing a specific antibody of predetermined specificity. Hybridomas secreting MAbs 11A25 and 11E32 MAb were selected after characterization of their biochemical and immunological properties for use in this invention as a mixture of antibodies to capture REV antigen.

The ELISA procedure is a double antibody sandwich test. A mixture of MAb 11A25 and 11E32 is used as the first antibody in coating microtiter plate wells, beads, or other solid substrate for the purpose of capturing REV antigen in the subsequently applied test material. The second antibody is the rabbit anti-REV polyclonal serum used as detection antibody. It is preferably supplemented with any commerically available anti-rabbit IgG as an indicator antibody and a substrate for color development.

When REV infection in chickens is suspected to be marginal, antigens from plasmas of infected chickens can be amplified in cell culture and tested by the ELISA described herein. The replication time required to reach endpoint titration of one infectious REV in cell culture is about 7-8 days.

Antibodies from plasmas of infected chickens can also be tested directly using the ELISA of the invention. The procedure employed is substantially the same as that described above for detecting REV antigen. For detection of the chicken antibody to REV, commercially available anti-chicken IgG conjugated to horseradish peroxidase is suitable as indicator antibody.

MAb 11E32 is cross-reactive at high affinity with all three subtypes of REV, e.g., subtype 1, strain T; subtype 2, DIAV and SN; subtype 3, CSV. This MAb recognizes a different epitope from MAb 11A25 which is also subtype common antibody. MAb 11E32 and MAb 11A25 are unreactive against Marek's disease and avian leukosis viruses. As previously stated, both MAb 11A25 and 11E32 immunoprecipitate REV envelope glycoprotein gp 62, recognize multiple epitopes on this glycoprotein, and produce synergistic reactivity in ELISA. The lower limit of gp 62 detection is about 120 ng of REV protein. Both antibodies are capable of reacting in an ELISA assay with cell-free virus and REV-infected cells.

The following examples are intended only to further illustrate the invention and are not intended to limit the scope of the invention which is defined by the claims.

EXAMPLE 1

Hybridoma Production

Propagation and purification of REV for immunization

Cloned nondefective REV strain T and strain CS were propagated in chicken embryo fibroblasts (CEF). Culture fluids were collected every other day and centrifuged at 21,000 rpm for 45 min using a "Beckman SW 27" rotor in a Model L2-65B ultracentrifuge. Virus was purified through a continuous sucrose gradient, and the purity of the preparation was verified by electron microscopy.

Immunization

Inbred BALB/c mice were immunized intraperitoneally (IP) with 0.5 mg of purified virions of REV strain T or with $2 \times 10^7$ REV-T infected CEF, prepared as described in Example 1. The mice were reimmunized after 28 days, followed by another IP boosting immunization 21 days later. Three days after the final immunization, spleens were removed and cells suspended in 5 ml Dulbecco's modified eagle medium (DMEM).

Fusion

Myeloma cells were fused with REV-immunized spleen cells at a ratio of 5:1. Fusion procedures and cell culture conditions were according to the methods of Lee et al. [J. Immunol. 130: 1003-1006 (1983)], herein incorporated by reference. The hybrid cells were dispensed into 96-well "Costar 3524" tissue culture plates. Beginning at about day 8-12, the hybridoma culture supernatant medium from wells showing cell growth was screened for antibody activity against strain T-infected CEF (T-CEF) or purified strain T virus by indirect ELISA.

Selection of hybridoma by indirect ELISA was conducted using microtiter plates coated with $3-4 \times 10^4$ REV-CEF or normal CEF per well by centrifugation, or coated with 200 ng of sucrose gradient purified virus. A 0.1-ml amount of hybridoma culture supernatant was added to REV-coated plates and incubated for 1 hr at 37° C. followed by washing three times with phosphate buffer saline (PBS) in 0.1% Tween-80. A 0.1-ml amount of anti-mouse IgG(H+L)-peroxidase conjugate (Miles Scientific, Naperville, Ill.) in a dilution of 1:1,000 with 3% BSA was added to the wells and incubated for another hour at 37° C. Wells were washed three times to remove unbound conjugate followed by adding 0.1 ml of freshly made substrate (0.08% aminosalicylic acid and 0.005% hydrogen peroxide in 0.02M phosphate buffer, pH 6.0). Absorbencies were measured in a 405 nm ELISA minireader. Two MCAs, 11A25 and 11E32, which were specific for a 62-kd protein and cross-reactive with REV strain T and CS but against different epitopes were selected as capture antibodies.

Expansion

Hybridomas that produced antibody positive for REV were transferred into 24-well plates for cell expansion and further testing against strain CS-infected CEF (CS-CEF) or purified strain CS virus for strain specificity. Hybridomas producing antibodies of interest were cloned by limiting dilution in 96-well plates.

Ascitic fluid was produced by IP injection of $3 \times 10^6$ cells from each cloned hybridoma into BALB/c mice primed 10-14 days previously with 0.3 ml of pristane (2,6,10,14-tetramethyl pentadecane, Aldrich Chemical Co., Milwaukee, Wis.). Ascitic fluids were harvested, clarified by centrifugation, and tested for antibody titers by endpoint dilution in ELISA and immunofluorescence (IF).

EXAMPLE 2

Preparation of polyclonal anti-REV rabbit serum for use in ELISA

About 2 mg sucrose-gradient purified strain T REV virus protein was emulsified 1:1 v/v in Freund's complete adjuvant and injected subcutaneously at multiple sites at the back of a rabbit. Twenty-one days later, three more booster shots with the same amount of virus protein in Freund's incomplete adjuvant were administered in 2-wk intervals. Two weeks after the final immunization, rabbits were bled, and serum was separated. The hyperimmunized anti-REV antiserum was absorbed with normal CEF cells and acetone-dried chicken liver powder to remove antibodies to normal CEF. The absorbed antiserum gave an endpoint titer of 1:4,000-6,000 in ELISA against REV-CEF.

EXAMPLE 3

Monoclonal antibody-mediated ELISA detection of REV antigen in infected chicken plasma Regional Poultry Research Laboratory line $7_1$ chicks were infected at 1 day of age with 1 ml of REV strain T. Two to three chickens from each group were bled 8-36 days after infection, and plasmas were collected by centrifugation and tested for REV antigen in four different assays: ELISA, IF, complement fixation (CF), and agar gel precipitation (AGP). The ELISA was conducted as described below.

A mixture of MAbs 11A25 and 11E32 (0.1 ml) at a dilution of 1:1,000 in 0.5M carbonate buffer, pH 9.5, was used to coat the wells of "Immulon I" microtiter plates (Dynatech, Alexandria, Va.) overnight at room temperature. Plates were washed once with PBS, air dried, and kept at 4° C. until use. To detect REV antigen, 0.1 ml of plasma was added to wells of microtiter plate precoated with MAbs. Plates were incubated for 2 hrs at room temperature and washed three times with 0.1% "Tween-80" in PBS. A 0.1-ml amount of absorbed anti-REV rabbit serum, prepared as in Example 2 and diluted 600-fold, was added to each well. After incubation for 1.5-2 hrs at room temperature, plates were washed three times with PBS-0.1% "Tween 80" to remove unbound rabbit serum. A 0.1-ml amount of anti-rabbit IgG peroxidase conjugate (Miles Scientific, Naperville, Ill.) at a dilution of 1:800 in 3% bovine serum albumin (BSA) was added, and plates were incubated for another 1.5-2 hrs at room temperature. Finally, 0.1 ml of freshly made substrate (0.08% aminosalicyclic acid and 0.005% hydrogen-peroxide in 0.02M phosphate buffer, pH 6.0) was added to each well. The absorbence was recorded after 30 min with an automatic ELISA reader.

The endpoint titers in ELISA ranged from 1:8 to 1:1000. Antigen was not detected by direct CF or AGP tests from all plasma samples. It was detected, however, by IF test only when the samples were cultured in chicken cells for 7-10 days.

EXAMPLE 4

Detection of REV antigen in egg albumen

Eggs were obtained from $15 \times 7$ hens infected with REV strain CS as 1-day-old embryos. For detection of REV antigen in albumen, 0.1 ml of undiluted albumen in duplicates were used in the ELISA described in Example 3. The results established that the ELISA was able to readily detect the antigen in egg albumen from all 24 eggs by six infected hens with viremia. Eggs from seven SPF hens gave negative values as expected.

EXAMPLE 5

Detection of REV antibodies in chicken serum

A mixture of MAbs 11A25 and 11E32 (0.1 ml) at a dilution of 1:1,000 in 0.5M carbonate buffer, pH 9.5 was used to coat the wells of "Immulon I" microtiter plates. Supernatant antigen (0.1 ml) was added to the precoated wells, and the plates were incubated overnight at 4° C. Remaining liquid in the wells was removed and 0.1 ml of test chicken serum diluted in 3% BSA was added to each well and incubated at room temperature for 2 hrs. The wells were again emptied, and the plates were washed three times with 0.1% "Tween-80" in PBS. One-tenth milliliter of goat antichicken globulin conjugated to horseradish peroxidase diluted 1:2,000 was added to each well and incubated for 90 min at room temperature. Finally, 0.1 ml of freshly made substrate (0.08% aminosalicyclic acid and 0.005% hydrogen-peroxide in 0.02M phosphate buffer, pH 6.0) was added to each well. The absorbence was recorded after 30 min with an automatic ELISA reader.

Results from multiple test sera showed that REV positive sera gave high titer of antibody with end point titers of 1:102,400. All negative sera tested were negative for REV antibodies.

EXAMPLE 6

Competitive inhibition ELISA for epitope mapping

Ascitic fluid was purified by precipitation twice with an equal volume of saturated ammonium sulfate and dialyzed against PBS overnight at 4° C. Purified IgGs thus obtained were used as competing MCAs as well as for conjugating with horseradish peroxidase (Sigma Chemical Company, St. Louis, Mo.). For the competition experiment, 100 $\mu l$ of purified MAbs in different concentrations in PBS were first added into wells precoated with sucrose-gradient purified REV strain T and incubated for 1 hr at 18° C. Plates were washed once with PBS. One hundred $\mu l$ of different MCA-conjugates diluted in 3% BSA were added and incubated for 1 hr at 18° C. The remaining procedure followed that of the ELISA described above. A series of reciprocal competition experiments was carried out. MAb 11A25 reacted to a type-common epitope, while MAbs 11E32 and 11C237 recognized a different common epitope. In addition, MAb 11E32 reacted synergistically with MAb 11A25. These results indicate that MAb 11A25 and 11E32 can be used in combination with one another in ELISA to enhance sensitivity of the test.

EXAMPLE 7

Immunoprecipitation and gel electrophoresis

REV-T- or CS-infected CEF cultures were labeled with medium containing 50 $\mu Ci/ml$ of [$^{35}S$]methionine or [³H]glucosamine, 50 μCi/ml, for 4–6 hrs. The labeled cells were lysed in buffer containing 150 mM NaCl, 1% sodium dodecyl sulfate (SDS), and 10 mM Tris-HCl, at pH 7.5. The Cowan I strain of *Saphylococcus aureus* was used for immunoprecipitation, and a 7.5–20% SDS-polyacrylamide linear gradient gel was prepared for electrophoresis.

The type-common MAb 11E32 immunoprecipitated a virus protein with molecular weight of 62K from [³⁵S]methionine labeled REV-CEF lysates. MAb 11A25 immunoprecipitated two viral specific proteins (62 and 21K) from T-CEF and CS-CEF. Both MAbs 11A25 and 11E32 recognized a T/CS strain-common epitope. The rabbit anti-REV immunoprecipitated six viral specific proteins from both strains T and CS, ranging in molecular weight from 21K to 62K. The polyclonal serum was not effective for distinguishing the T and CS strains. To further characterize the three polypeptides, REV was labeled with [³H]glucosamine. The results showed that the MAbs immunoprecipitated 62K and 21K glycoproteins.

EXAMPLE 8

Specificities of cloned MAbs in ELISA

The titers of MAb 11A25, MAb 11E32, and MAb 11C237 were compared in ELISA as described above in Example 3 against REV-T, CSV, and DIAV in infected CEF culture supernatant. Of the three monoclonal antibodies, MAb 11A25 gave the highest ELISA titer. As shown in Table I, below, MAb 11E32 showed better ELISA titer and has a broader range of reactivity than MAb 11C237 against the three REV subtypes. When these MAbs were compared in ELISA against Marek's disease virus (MDV)-infected CEF, avian lymphoid leukosis virus (LLV)-infected CEF and normal CEF cultures, reactions were negative.

EXAMPLE 9

Specificities of cloned MAbs in fluorescent antibody test

Thirty five-mm plates with growing CEF cells were inoculated with 2 ml of infected CEF-supernatant or chick plasma diluted from 10-1 to 10-4 in CEF medium and incubated at 37° C. for 2 hrs. The inocula were then aspirated from the plates and 2 ml of CEF media with 0.6% agar at 50° C. were used to cover the CEF monolayer. Plates were incubated for 1 wk at 37° C. This was followed by removal of agar gel from plates and the addition of 1 ml of cold alcohol-acetone (4:6) mixture to fix CEF monolayer for 2 min. The alcohol-acetone mixture was poured off. The cell monolayer was allowed to dry naturally. Approximately 1–2 ml of MAb 11A25 or 11E32 in PBS at a dilution of 1:400 was added and the plates was incubated for 1 hr at 37° C. After washing with PBS, 1 ml of fluorescein isothiocyanate conjugated anti-mouse IgG (Miles-Yeda Ltd., Rehovot, Israel) at a dilution of 1:20 in PBS was added and incubated for 40 min at 37° C. Plates were washed three times with PBS to remove unbound conjugate. Florescent foci were viewed with an IF microscope.

The titers of MAb 11A25, MAb 11E32, and MAb 11C237 were compared in FA as described above against the same three REVs assayed by ELISA in Example 8. These MAbs, which reacted in high titers with strains of REV in ELISA, also cross-reacted in IF.

TABLE I

| Titers of MAbs to Different REV Strain-Infected CEF | | | |
|---|---|---|---|
| MCAs | REV-T | CSV | DIAV |
| 11A25 | $10^5$ | $10^5$ | $10^5$ |
| 11C237 | $5.4 \times 10^3$ | $1.3 \times 10^4$ | 10 |
| 11E32 | $6.4 \times 10^3$ | $2.5 \times 10^4$ | $6.4 \times 10^3$ |

We claim:

1. The hybridoma cell line ATCC HB 10441 or subcultures thereof.

2. Monoclonal antibody 11E32 produced by the cell line of claim 1.

3. A component of a MAb-mediated ELISA kit for detection of avian reticuloendotheliosis virus antigens or antibodies comprising a solid substrate coated with monoclonal antibody 11E32.

4. An ELISA kit component as described in claim 3 wherein said substrate in additionally coated with monoclonal antibody 11A25.

5. An ELISA kit component as described in claim 4 wherein said substrate is a microtiter plate.

6. A method for detecting avian reticuloendotheliosis virus (REV) antigen or antibody in a biological sample of avian origin comprising assaying said sample in a monoclonal antibody-mediated immunoassay comprising the following steps:

a. binding the monoclonal antibody 11E32 to a solid substrate;
   b. contacting the bound antibody of step (a) with a first component comprising REV antigen under conditions which allow the antigen to bind to said antibody;
   c. contacting the bound REV antigen from step (b) with a second component comprising anti-REV antibody under conditions which allow the anti-REV antibody to bind to the antigen;
   d. contacting the bound anti-REV antibody from step (c) with a reactive indicator under conditions which allow the indicator to bind to the anti-REV antibody; and
   e. subjecting said bound indicator from step (d) to conditions which allow visualization thereof;

wherein the biological sample is the source of the first component in a method for detecting REV antigen and the biological sample is the source of the second component in a method for detecting REV antibody.

7. The method of claim 6 and further comprising binding the monoclonal antibody 11A25 to the solid substrate in step (a).

8. The method of claim 6 wherein the biological sample is the source of REV antigen in step (b).

9. The method of claim 6 wherein the biological sample is the source of the anti-REV antibody in step (c).

* * * * *